United States Patent [19]

Hornberger, Sr.

[11] Patent Number: 5,593,641

[45] Date of Patent: Jan. 14, 1997

[54] SCULPTURED AIR FRESHENER DISPENSER

[76] Inventor: Frederick C. Hornberger, Sr., 62 Flamingo St., New Orleans, La. 70124

[21] Appl. No.: 517,922

[22] Filed: Aug. 22, 1995

[51] Int. Cl.$^6$ .............................. A61L 9/14; B05B 11/02
[52] U.S. Cl. ........................ 422/123; 422/120; 222/78; 222/183; 239/211
[58] Field of Search .................................. 422/120, 123; 222/78, 183; 239/34, 211, 331; 220/300

[56] References Cited

U.S. PATENT DOCUMENTS

| | | | |
|---|---|---|---|
| D. 285,961 | 9/1986 | Pennell | D23/150 |
| D. 298,772 | 11/1988 | Verri | D23/367 |
| D. 336,332 | 6/1993 | Woolley | D23/367 |
| 3,184,115 | 5/1965 | Meshberg | 222/183 |
| 3,369,691 | 2/1968 | Wei | 220/300 |
| 3,420,412 | 1/1969 | Greene | 222/78 |
| 3,432,077 | 3/1969 | Voll | 222/78 |
| 3,914,805 | 10/1971 | Dolan | 4/227 |
| 4,277,004 | 7/1981 | Barlics | 222/402.14 |
| 4,889,284 | 12/1989 | Spector | 239/211 |
| 5,456,626 | 10/1995 | Ming-Kang | 222/78 |
| 5,458,263 | 10/1995 | Ciammitti et al. | 222/183 |

*Primary Examiner*—Robert J. Warden
*Assistant Examiner*—Theresa T. Snider
*Attorney, Agent, or Firm*—Joseph N. Breaux

[57] ABSTRACT

A sculptured air freshener dispenser of the type having a sculptured shell concealing a canister of air freshener or disinfectant therein is provided. The sculptured air freshener dispenser includes: a sculptured shell defining an interior cavity, a canister of pressurized air freshener having a stem for releasing the air freshener, and a dispensing mechanism disposed within the interior cavity of the sculptured shell in functional connection with the canister. The dispensing mechanism includes: a housing defining a chamber therein accessible through the sculptured shell, the canister being removably held within the chamber; a plunger having a first end accessible from exterior the sculptured shell, the plunger defining a fluid passage in connection between a first end port and a second port, the first end port in fluid connection with the stem; and a flexible hose defining a fluid pathway in connection between an initial end opening in fluid connection with the second port and a terminal end opening disposed through the sculptured shell.

1 Claim, 3 Drawing Sheets

SCULPTURED AIR FRESHENER DISPENSER

TECHNICAL FIELD OF THE INVENTION

The present invention relates to devices for dispensing air freshener and more particularly to devices for dispensing air freshener that conceal the source of air freshener within a sculptured shell.

BACKGROUND OF THE INVENTION

Typically, air freshener or disinfectant is dispensed within bathrooms, playrooms, offices and the like by use of hand held canisters. After use the canister has to be stored and is often lost or not readily available when needed. In many commercial locations devices are used that automatically dispense air freshener or disinfectant at predetermined timed intervals. However, these devices require installation and are expensive and inefficient when air freshener or disinfectant is only needed on a periodic random basis.

It would be a benefit, therefore, to have a sculptured air freshener dispenser which is attractive and that conceals a canister of pressurized air freshener or disinfectant in a sculptured shell. It would be a further benefit, to have a sculptured air freshener dispenser that provides for easy removal and replacement of canisters of air freshener or disinfectant. It would be an additional benefit, to have a sculptured air freshener dispenser that uses standard inexpensive commercial type canisters of air freshener or disinfectant.

SUMMARY OF INVENTION

It is thus an object of the invention to provide a sculptured air freshener dispenser that conceals a canister 0f air freshener or disinfectant and the corresponding dispensing mechanism within a sculptured shell.

It is a further object of the invention to provide a sculptured air freshener dispenser that has a dispensing mechanism operable from exterior the sculptured shell.

It is a still further object of the invention to provide a sculptured air freshener dispenser that provides for easy removal and replacement of canisters of air freshener or disinfectant.

Accordingly, a sculptured air freshener dispenser of the type having a sculptured shell concealing a canister of air freshener or disinfectant therein is provided. The sculptured air freshener dispenser comprises: a sculptured shell defining an interior cavity, a canister of pressurized air freshener having a stem for releasing the air freshener, and a dispensing mechanism disposed within the interior cavity of the sculptured shell in functional connection with the canister. The dispensing mechanism includes: a housing defining a chamber therein accessible through the sculptured shell, the canister being removably held within the chamber; a plunger having a first end accessible from exterior the sculptured shell, the plunger defining a fluid passage in connection between a first end port and a second port, the first end port in fluid connection with the stem; and a flexible hose defining a fluid pathway in connection between an initial end opening in fluid connection with the second port and a terminal end opening disposed through the sculptured shell.

The shell may be made of ceramic, plastic, wood or any other material which may be sculptured and shaped. The shell may be sculptured to resemble various objects such as rabbits, fish, angels, flowers, candles or others as appropriate for the room in which the sculptured air freshener dispenser is to be used. The sculptured shell defines an interior cavity of sufficient size to dispose a canister of air freshener or disinfectant and the dispensing mechanism. The sculptured shell forms an opening for disposing a terminal end opening of the flexible hose for exhausting air freshener.

The housing member is accessible through the sculptured shell for removing or replacing the canister. The shell may have a section removable for accessing the housing. The shell may define an opening adjacent to the housing.

The plunger has a first end accessible from the exterior of the sculptured shell. The shell may define a hole for disposing the first end of the plunger or for disposing a finger for depressing the plunger. The shell may have a pliable section, such as rubber, formed adjacent to the first end of the plunger which may be depressed a sufficient distance in order to depress the plunger releasing the air freshener.

The housing may be formed of any material suitable for rigidly holding the canister of air freshener or disinfectant such as plastic, metal or ceramic. The housing defines a chamber for removably holding the canister. The housing provides an access to the chamber such as a hinge section or a cap lockably disposable in a aperture defined by the housing. The housing forms an aperture for disposing the stem of the canister.

The plunger is elongated having a first end accessible from exterior the sculptured shell and a second end in functional connection with the stem. The second end may be a first port end in connection with a fluid passage. A return mechanism may be in connection with the plunger to return the plunger to a first set position after the plunger has been depressed and released.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

DETAILED DESCRIPTION OF THE PREFERRED EMBODIMENT

Figure 1:
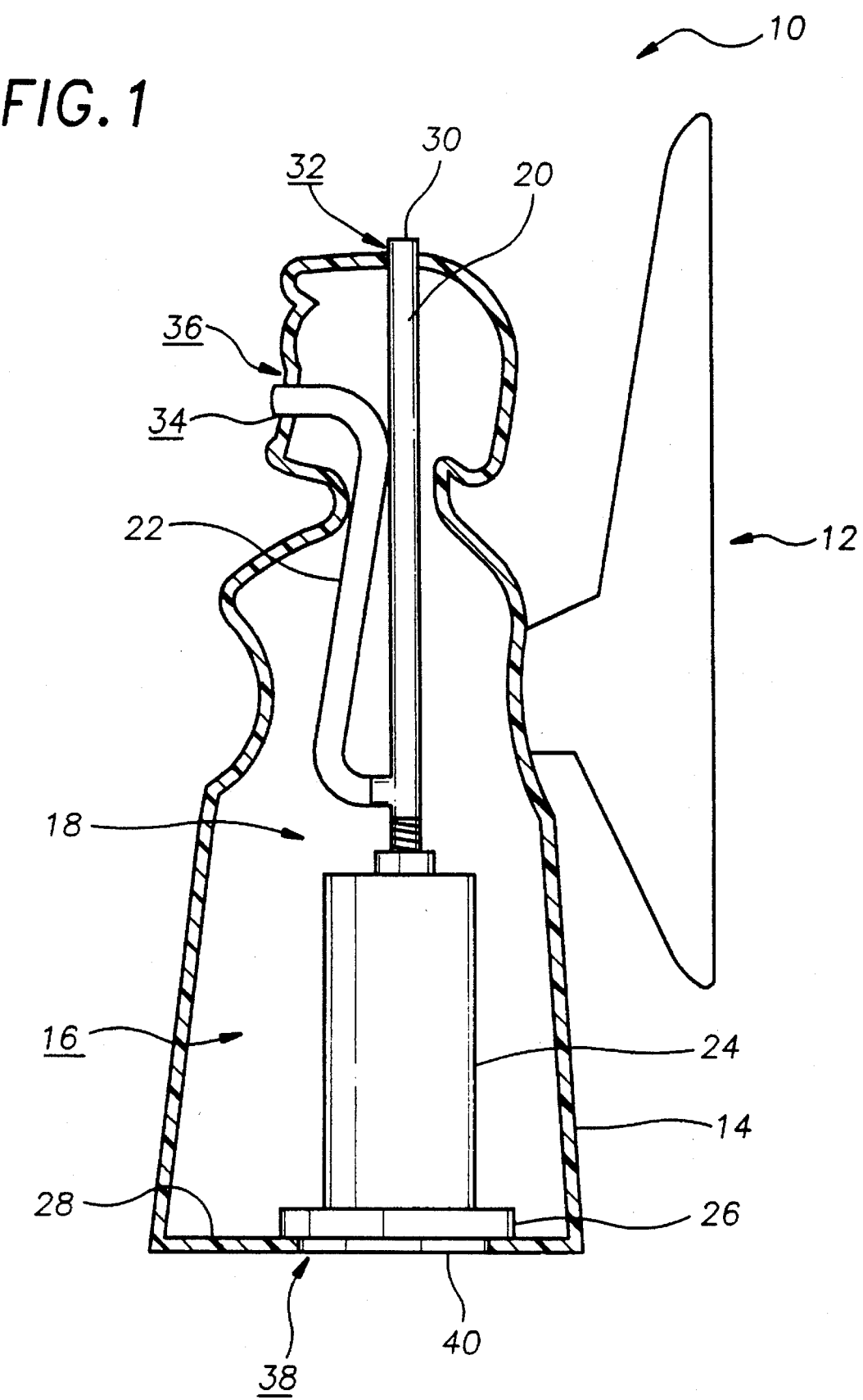
FIG. 1 is a sectional, side view of an exemplary embodiment of the sculptured air freshener dispenser of the present invention.

FIG. 1 is a sectional, side view of an exemplary embodiment of the sculptured air freshener dispenser of the present invention generally designated by the numeral 10. Sculptured air freshener dispenser 10 includes a sculpture generally designated 12 having a sculptured shell 14 defining an interior cavity 16, and a dispensing mechanism generally designated 18 having a plunger 20, a flexible hose 22 and a housing 24 for removably holding a canister of pressurized air freshener (not shown) therein.

As shown, shell 14 is made of ceramic and is sculptured to define an angel having wings. Shell 14 defines an interior cavity 16 having a size sufficient to dispose dispensing mechanism 18. Base 26 of housing 24 is connected to an interior surface 28 by glueing.

Plunger 20 has a first end 30 movable disposed through a first opening 32 defined by shell 14. Flexible hose 22 has a terminal end opening 34 disposed through a second opening 36 defined by shell 14. Terminal end 34 is rigidly connected to shell 14 within second opening 36 by glueing. Shell 14 defines a third opening 38 concentrically aligned with housing 24. A cap 40 removably connected to housing 24 is disposed in third opening 38.

Figure 2:
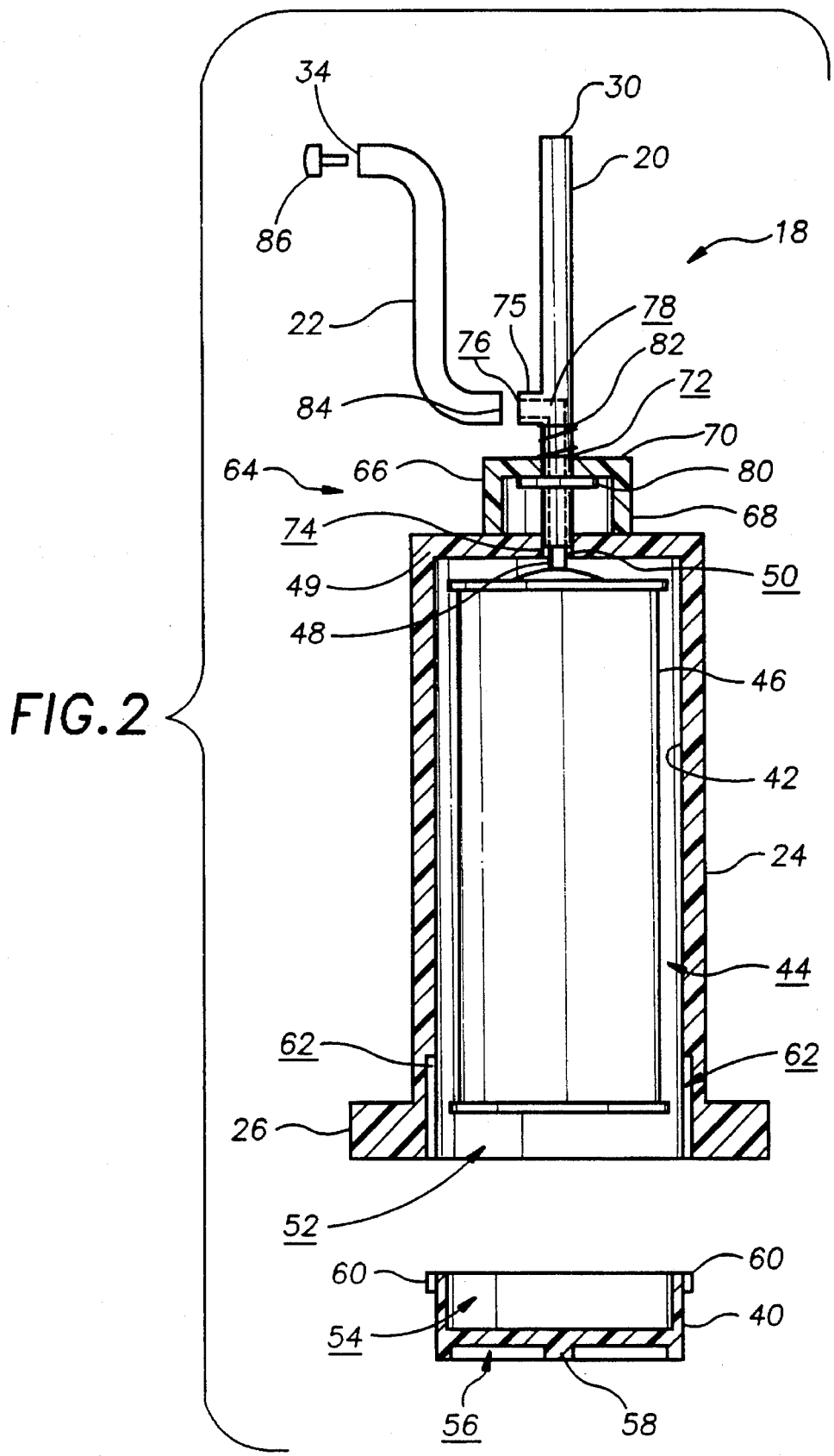
FIG. 2 is a sectional, side view of the dispensing mechanism.

FIG. 2 is a sectional, side view of dispensing mechanism 18. Housing 24 is concentric and formed of a rigid plastic of unitary construction. Housing 24 has a inner surface 42 defining a chamber 44 sized to removably dispose a conventionally sized canister 46 of air freshener, having a stem 48, therein. Top section 49 of housing 24 defines a top aperture 50 therethrough for passing stem 48. Base 26 forms a base aperture 52 for inserting and extracting canister 46 from chamber 44.

Canister 46 is removably held in place by cap 40. Cap 40 defines a first recess 54 for disposing the bottom portion of canister 46. Cap 40 defines a second recess 56 having a rib 58 therein for a user to grasp and rotate cap 40. Two pegs 60 extend from cap 40 for inserting in L-shaped slots 62 defined by inner surface 42 of housing 24 for removably locking cap 40 within base aperture 52.

A U-shaped bracket generally designated 64 having a first and second leg 66,68 extending perpendicularly from a planar member 70 is mounted on top section 49 of housing 24. Planar member 70 defines a hole 72 therethrough for slidably disposing plunger 20.

Plunger 20 is a rigid elongated member formed of plastic having a first end 30, a first end port 74 and a second port 76. Plunger 20 defines a fluid passage 78 (denoted by the broken lines) therein in connection between first end port 74 and second port 76. Second port 76 is defined by an arm 75 extending perpendicularly from plunger 20 between first end 30 and first end port 74.

First end port 74 is slidably disposed through hole 72 of bracket 64 and detachably connected to stem 48. A flange 80 is rigidly connected about plunger 20 between planar member 70 of bracket 64 and first end port 74. A helical spring 82 is attached about plunger 20 between arm 75 and planar member 70 for urging first end 30 of plunger 20 away from housing 24.

Flexible hose 22 is formed of rubber and defines a fluid pathway (not shown) in connection between an initial end opening 84 and a terminal end opening 34. Initial end opening 84 is fluidly connected to second port 76 by glueing to arm 75. A nozzle 86 is connected to terminal end opening 34.

Figure 3:
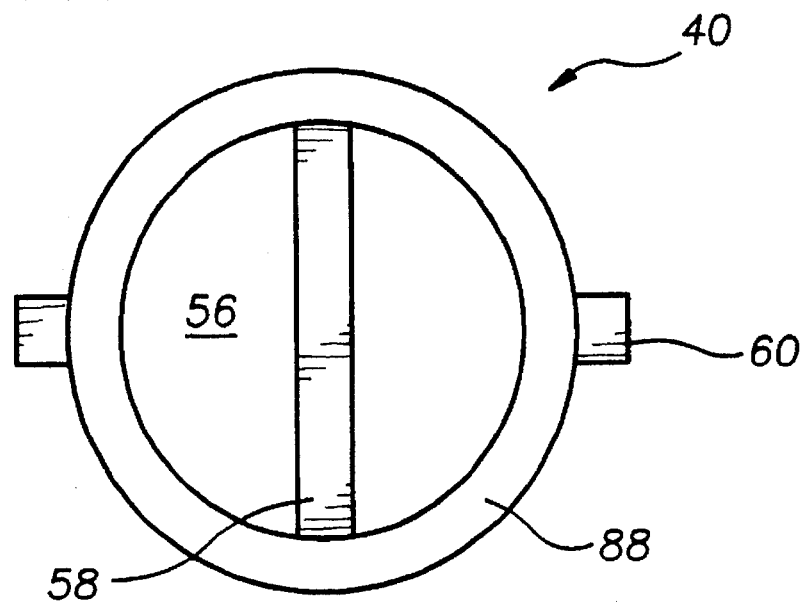
FIG. 3 is an end view of the cap.

FIG. 3 is an end view of cap 40. As shown, pegs 60 extend perpendicularly from outer ring 88. Rib 58 extends laterally across cap 40 within recess 56.

Figure 4:
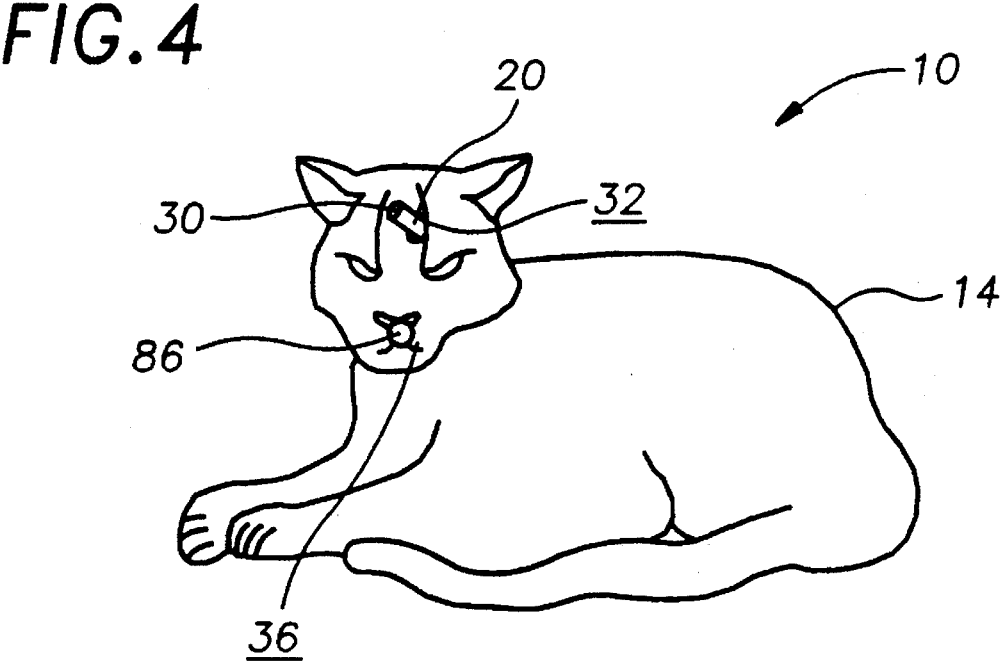
FIG. 4 is a plan view of another exemplary embodiment of the sculptured air freshener dispenser of the present invention.

FIG. 4 is a plan view of another exemplary embodiment of the sculptured air freshener dispenser of the present invention generally designated by the numeral 10. In this embodiment, shell 14 is made of ceramic sculptured to define a cat. First end 30 of plunger 20 is movably disposed through first opening 32 formed through shell 14. Nozzle 86 is shown disposed through second opening 36 of shell 14.

Use of the sculptured air freshener dispenser 10 is now described with reference to FIGS. 1–4. Rib 58 is rotated counter clockwise releasing pegs 50 from slots 62 allowing cap 40 to be removed from base aperture 52 of housing 24. A canister 46 of pressurized air freshener is then inserted into chamber 44, detachably connecting stem 48 to first port end 74 of plunger 20. Cap 40 is then lockably replaced by reversing the procedure for removal, holding canister 46 within chamber 44.

To release a burst of air freshener the user depresses first end 30 of plunger 20 compressing spring 82 and urging first port end 74 depressingly against stem 48 releasing air freshener from canister 46. The released air freshener passes through fluid passage 78 of plunger 20 and through the fluid pathway of flexible hose 22 exhausting from nozzle 86 as a fine mist. When the user releases pressure from first end 30 spring 82 expands urging first port end 74 from stem 48 stopping the release of air freshener. Flange 80 restrains the expansion of spring 82 by contacting planar member 70.

It can be seen from the preceding description that a device for dispensing air freshener which conceals a canister of air freshener or disinfectant and the corresponding dispensing mechanism within a sculptured shell, has a dispensing mechanism operable from exterior the sculptured shell, and that provides for easy removal and replacement of canisters of air freshener or disinfectant has been provided.

It is noted that the embodiment of the sculptured air freshener dispenser described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A sculptured air freshener dispenser comprising:

a sculptured shell defining an interior cavity and a top opening, a second opening and a third opening in connection with said interior cavity;

a canister of pressurized air freshener having a stem for releasing said air freshener;

a housing defining a chamber therein removably holding said canister, said housing having a base having a base aperture defined therein, said base being adhesively secured to an interior surface of said sculptured shell in a manner such that said base aperture is concentrically aligned with said third opening of said sculptured shell;

said housing having an inner surface defining an L-shaped slot adjacent said base aperture;

said housing having a top section defining a top aperture having said stem of said canister disposed therethrough;

a cap defining a first and second recess, said cap being lockably disposed within said base aperture, said first recess having a bottom portion of said canister disposed therein in a manner to hold said canister in said chamber;

a peg extending perpendicularly from said cap disposed in said L-shaped slot;

a rib extending laterally across said cap within said second recess;

a plunger having a first end passing through said top opening of said sculptured shell, said plunger defining a fluid passage in connection between a first end port and a second port, said first end port being in fluid connection with said stem;

an arm extending substantially perpendicular from said plunger defining said second port;

a U-shaped bracket extending from said top section of said housing, said U-shaped bracket having a first leg, a second leg and a planar member, said planar member defining a hole therethrough concentrically aligned with said top aperture, said hole having a portion of said plunger disposed between said arm and said first end port;

a helical spring positioned over a portion of said plunger located between said arm of said plunger and said planar member of said U-shaped bracket;

a flange connected about said plunger and positioned between said planar member and said first end port;

a flexible hose defining a fluid pathway in connection between an initial end opening in fluid connection with said second port and a terminal end opening disposed through said second opening of said sculptured shell; and a nozzle in fluid connection with said terminal end opening of said flexible hose for exhausting said air freshener as a mist.

\* \* \* \* \*